United States Patent
Frey et al.

(10) Patent No.: US 9,796,574 B2
(45) Date of Patent: Oct. 24, 2017

(54) AUTOMATED BIT EXCHANGE METHOD AND APPARATUS FOR LABORATORY SAMPLE TUBE CAPPING AND DECAPPING MACHINES

(71) Applicant: Hamilton Storage Technologies, Inc., Franklin, MA (US)

(72) Inventors: Martin Frey, Reichenburg (CH); Beat Thöny, Grüsch (CH); Beat Zahner, Kaltbrunn (CH); Petra Tappe, Chur (CH)

(73) Assignee: Hamilton Storage Technologies, Inc., Franklin, MA (US)

( * ) Notice: Subject to any disclaimer, the term of this patent is extended or adjusted under 35 U.S.C. 154(b) by 0 days.

(21) Appl. No.: 15/335,597

(22) Filed: Oct. 27, 2016

(65) Prior Publication Data

US 2017/0113909 A1    Apr. 27, 2017

Related U.S. Application Data

(60) Provisional application No. 62/246,716, filed on Oct. 27, 2015.

(51) Int. Cl.
*B67B 3/20* (2006.01)
*B67B 7/18* (2006.01)
(Continued)

(52) U.S. Cl.
CPC .......... *B67B 3/208* (2013.01); *B01L 3/50825* (2013.01); *B23Q 3/15506* (2013.01);
(Continued)

(58) Field of Classification Search
CPC .. B67B 1/06; B67B 3/20; B67B 3/204; B67B 3/2053; B67B 3/2066; B67B 3/208;
(Continued)

(56) References Cited

U.S. PATENT DOCUMENTS 3,566,516 A * 3/1971 Brainard et al. ... B23Q 3/15706
414/728
3,589,103 A * 6/1971 Calvillo et al. ....... B67B 3/2053
53/381.4
(Continued)

FOREIGN PATENT DOCUMENTS

CN    203653204 U    6/2014
CN    204125137 U    1/2015
(Continued)

OTHER PUBLICATIONS

International Search Report and Written Opinion in co-pending PCT Application PCT/US16/59006 dated Feb. 3, 2017.
(Continued)

*Primary Examiner* — Stephen F Gerrity
(74) *Attorney, Agent, or Firm* — Andrus Intellectual Property Law, LLP

(57) ABSTRACT

A laboratory capper, decapper or combination capper/decapper includes a deck containing with a nest designed to hold an SBS-formatted tube storage rack, and a bit exchange magazine assembly containing one or more sets of adapter bits. The adapter bits are mounted on and unloaded from motor driven fittings, and are exchanged in order to cap or decap laboratory sample tubes or vials that have different head configurations. The bit exchange magazine assembly enables the bit to be exchanged robotically.

16 Claims, 11 Drawing Sheets

(51) Int. Cl.
*G01N 35/04* (2006.01)
*B23Q 3/157* (2006.01)
*B23Q 3/155* (2006.01)
*B01L 3/00* (2006.01)

(52) U.S. Cl.
CPC ........ *B23Q 3/15786* (2013.01); *B67B 3/2053* (2013.01); *B67B 3/2066* (2013.01); *B67B 7/182* (2013.01); *B23Q 2003/15537* (2016.11); *B67B 2201/10* (2013.01); *G01N 2035/0405* (2013.01); *Y10T 483/1845* (2015.01)

(58) Field of Classification Search
CPC ....... B67B 7/02; B67B 7/182; B67B 2201/10; G01N 35/026; G01N 2035/00752; G01N 2035/00762; G01N 2035/00772; G01N 2035/0403; G01N 2035/0405; B23Q 3/15506; B23Q 3/15526; B23Q 3/15536; B23Q 3/15539; B23Q 3/15706; B23Q 3/15786; B23Q 2003/15537; Y10T 483/18; Y10T 483/1809; Y10T 483/1845; B01L 3/50825; B01L 3/5453
USPC ... 53/490, 492, 285, 287, 299, 331.5, 381.4; 483/16, 31, 37, 54, 55, 58, 59, 63, 64
See application file for complete search history.

(56) References Cited

U.S. PATENT DOCUMENTS

| | | | |
|---|---|---|---|
| 4,669,174 A | 6/1987 | Fischer et al. | |
| 5,821,407 A * | 10/1998 | Sekiguchi et al. | G01N 11/14 279/128 |
| 6,257,091 B1 | 7/2001 | Cohen et al. | |
| 7,845,149 B2 * | 12/2010 | Owen et al. | G01N 35/026 53/281 |
| 2002/0108857 A1 * | 8/2002 | Paschetto et al. | B01L 3/0244 204/457 |
| 2005/0265901 A1 | 12/2005 | Sinclair et al. | |
| 2007/0098597 A1 * | 5/2007 | Brunner | B01L 9/06 422/400 |
| 2008/0060719 A1 * | 3/2008 | Massaro | G01N 35/0099 141/237 |
| 2009/0056285 A1 * | 3/2009 | Kramer et al. | G01N 35/04 53/492 |
| 2013/0116102 A1 * | 5/2013 | Hansen | B04B 11/043 494/10 |
| 2014/0311090 A1 * | 10/2014 | Weber | B67B 7/182 53/381.4 |
| 2015/0175398 A1 * | 6/2015 | Christensen et al. | B67B 3/20 53/490 |
| 2016/0320423 A1 | 11/2016 | Hoffmann et al. | |

FOREIGN PATENT DOCUMENTS

| | | | | |
|---|---|---|---|---|
| DE | 3403915 A1 | * | 8/1985 | ........ B23Q 3/15533 |
| DE | 4028503 A1 | * | 3/1992 | ........ B23Q 3/15546 |
| DE | 102013114041 | | 6/2015 | |
| EP | 0312861 A1 | | 4/1989 | |
| EP | 1878549 A1 | * | 1/2008 | .......... B23B 31/008 |
| JP | 61038840 A | * | 2/1986 | ........ B23Q 3/15526 |
| JP | 62136351 A | * | 6/1987 | ........ B23Q 3/15526 |
| JP | 2012159317 A | * | 8/2012 | ............... G01N 1/00 |

OTHER PUBLICATIONS

Hamilton Storage Technolgies, LabElite I.D. Capper flyer, 2013, 2 pages.
Hamilton Storage Technologies, LabElite Integrated I.D. Capper flyer, 2014, 2 pages.

* cited by examiner

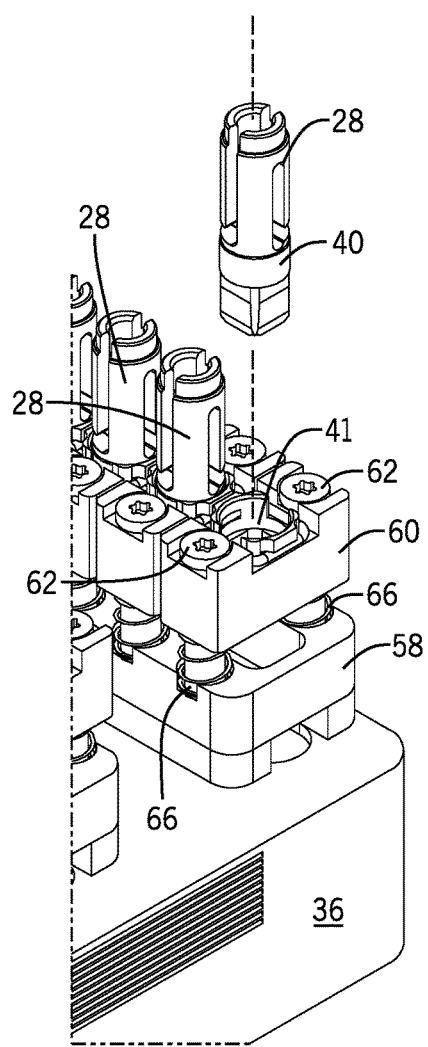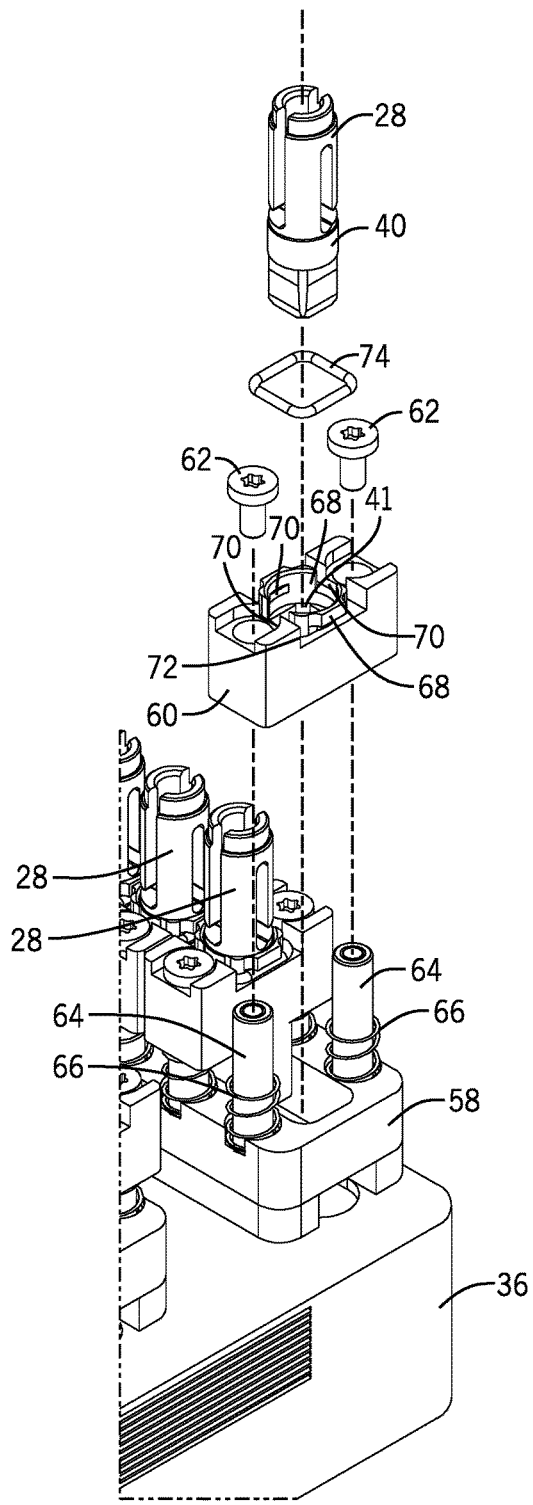
FIG. 5
FIG. 6

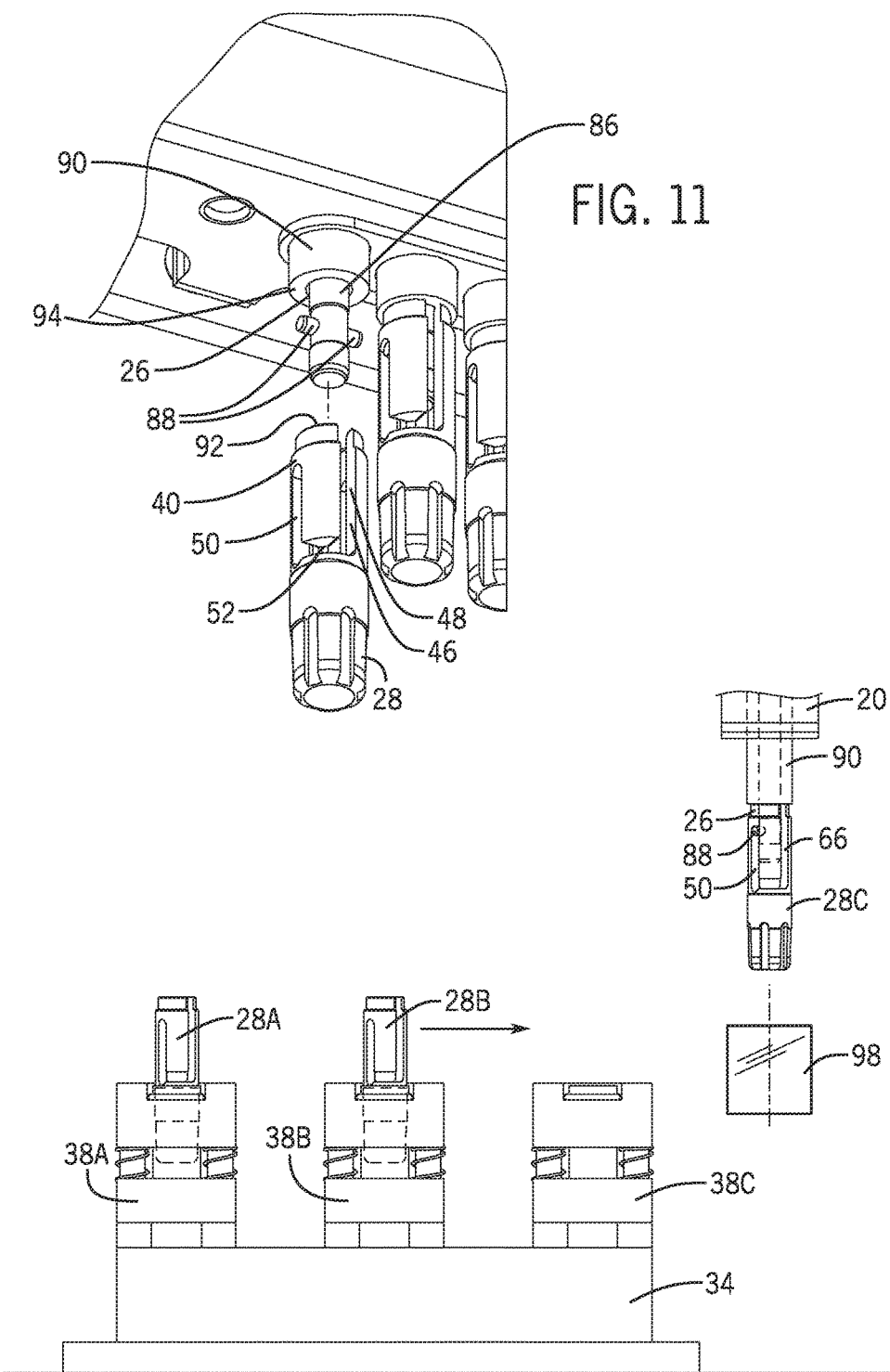

AUTOMATED BIT EXCHANGE METHOD AND APPARATUS FOR LABORATORY SAMPLE TUBE CAPPING AND DECAPPING MACHINES

FIELD OF THE INVENTION

The invention pertains to the exchange of adapter bits on benchtop instruments that automatically screw caps on or off of laboratory sample tubes.

BACKGROUND OF THE INVENTION

Laboratory sample tubes, sometimes called microtubes or cryovials, are normally stored in SBS-formatted storage racks. One of the most common sizes is a 96-tube storage rack which includes eight rows and twelve columns of tube receptacles for holding 96 sample tubes. SBS format standards petinent to tube storage racks are ANSI/SLAS 1-2004 (footprint dimensions, e.g., 85.48 mm ×127.76 mm) and ANSI/SLAS 4-2004 (well positions, e.g. 9 mm spacing for 8×12 well array). Storage racks designed to hold larger sample tubes typically hold 48 or 24 tubes. The sample tubes normally have screw caps to seal the top of tubes. A 2-D barcode is often printed on the bottom of the tubes for automated tracking purposes. Most storage racks contain openings in the bottom of the rack to enable a barcode reader to read the 2-D barcodes from below the rack.

Screw caps on sample tubes can be removed manually but this is a tedious process. Therefore, robotic machines have been designed to automatically screw caps on or screw caps off of sample tubes when the tubes are held in a tube storage rack. This kind of robotic machine is known as a capper, a decapper, or a combined capper/decapper. The machines typically include a header with spaced-apart, rotatable fittings designed to engage the head of respective caps in a row of sample tubes in an SBS-formatted storage rack placed in a nest below the header. To remove caps, the header is lowered robotically so that the fittings, or bits on the fittings, engage the heads of the respective cap for a row of tubes. The bits seat within the head of the respective cap and then turn the caps simultaneously by rotating the fittings counterclockwise. After the caps are removed from tubes on a source rack, they are normally placed in an array on another rack that serves as a cache for the caps. After the samples in the open tubes have been used, the caps on the cache rack are then screwed back on to the respective tubes in a similar fashion.

There are several sample tube manufacturers and it is not uncommon for these manufacturers to each have a unique head configuration for the screw cap. Present day laboratories tend to use several labware manufacturers, opting to implement various forms of research with different brands of microtubes or sample tubes, each with specific advantages for a given application. Since there are a wide variety of such configurations, some capper and decapper systems have removable adapter bit sets for the rotating fittings on the header. These adapter bit sets are typically manually removed and replaced with another bit set when it is desired to remove or place caps on a different brand of sample tubes. The process of exchanging adapter bits is also time-consuming.

SUMMARY OF THE INVENTION

The invention pertains to the use of an SBS-formatted bit exchange magazine that enables the automated replacement of adapter bits on a laboratory capper, decapper or combination capper/decapper. With the invention, adapter bits are exchanged more quickly and reliably.

In one aspect of the invention, the capper, decapper or combination capper/decapper includes a deck containing at least one nest designed to hold an SBS-formatted tube storage rack, and a bit exchange magazine assembly containing one or more sets of adapter bits. The bit exchange magazine assembly also has an SBS-formatted footprint that can be set into the nest. This enables the apparatus normally used to cap and decap to also automatically exchange bit sets. The nest is oriented so that a tube storage rack set in the nest has rows of tube receptacles parallel to each other and extending in a first direction. The header located above the deck is also oriented parallel to the first direction. The header is capable of moving vertically up and down with respect to the deck. Multiple fittings for mounting a set of adapter bits are located on the header. Each adapter bit, when mounted on a fitting, is configured to engage a head of a cap for a laboratory sample tube and turn the cap with respect to the sample tube when the sample tube is in a rack positioned in the nest under the header. The multiple fittings and adapter bits mounted on the fittings (and any cap engaged by the respective bit) are turned, preferably by individual torque sensing motors. For the same capper/decapper instrument to be used to automatically exchange adapter bits, the bit exchange magazine assembly with an SBS-formatted footprint is set in the nest instead of the tube storage rack. The magazine assembly includes at least one bit magazine but desirably at least three bit magazines, each containing a row of bit receptacles. The rows of bit receptacles on the magazine assembly are arranged to be parallel with the first direction when the magazine assembly is set in the nest.

The bit receptacles on the magazines in the exemplary embodiment of the invention are configured to hold adapter bits having different head configurations and sizes, and also different torso lengths. The configuration of the bit collars are uniform, however, to facilitate automated mounting on and unloading from the header fittings. The bit receptacles in the magazines include a retention clasp that holds the torso of the adapter bits from rotating or from falling out when the adapter bits are fully inserted into the receptacles. The receptacles also include sufficient space below the retention clasp to accommodate a wide variety of bit torso and head configurations.

To use the instrument to exchange a row of adapter bits, adapter bits that are installed on the row of fittings on the header are off-loaded into one of the rows of bit receptacles on the magazine assembly and a selected new set of adapter bits are loaded or mounted onto the fittings from a neighboring row of bit receptacles. The rows of bit receptacles contain labware specific bit sets which can be loaded onto the magazine as the user wishes. Automatic identification of the individually stored bit sets is possible using, for example, an onboard laser sensor and reflector strips to create a binary code read by the firmware on the device.

In one exemplary embodiment, each of the fittings on the header includes a spring and pin mechanism for mounting or unloading the respective bit sets. The bits in this embodiment have a collar with pin receiving channel. The pin receiving channel has a locking portion that is rotationally offset from a slot that is accessible from the top rim of the collar vertically downward. At the bottom of the slot, the channel extends rotationally around the collar to the offset locking portion of the channel. Desirably, the locking portion of the channel extends upward, but not to the upper rim, in order to secure the pin on the fitting in a reliable locked position. A spring biased sleeve around the fitting pushes downward on the bit collar and biases the pin against the top of the locking portion of the channel to securely lock the bit in place when it is rotated into the locked position. To release the bit, the fitting is pushed downward against the spring bias, rotated and lifted so that the pin and the fitting clear the upper rim of the bit. The spring bias helps to release the bit from the fitting, and the retention clasp on the magazine holds the adapter in the bit receptacle on the magazine. These steps are implemented by automated control of the motion of the header and the fittings using the receptacles in the bit exchange magazine to reliably hold the adapter bits as necessary.

Other aspects and advantages of the invention may be apparent to those skilled in the art upon reviewing the drawings and the following description thereof.

BRIEF DESCRIPTION OF THE DRAWINGS

FIG. 5 is a perspective view of a portion of the bit exchange magazine assembly shown in FIGS. 2 and 3.

FIG. 6 is a view similar to FIG. 5 showing parts of the bit exchange magazine assembly exploded away.

FIG. 11 is a perspective view illustrating a fitting on a header of the apparatus shown in FIG. 2 an exemplary adapter bit.

FIGS. 12A through 12G illustrate steps for automatically changing an adapter bit on the apparatus shown in FIG. 2.

DETAILED DESCRIPTION

Figure 1:
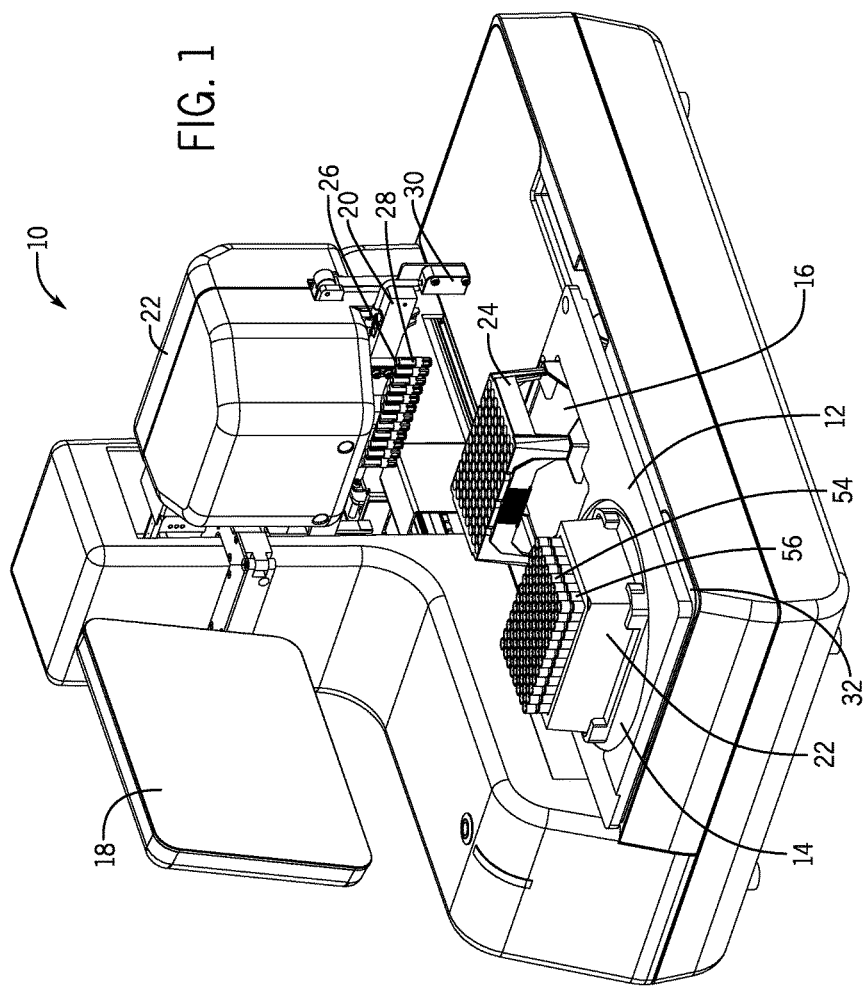
FIG. 1 is a perspective view of an automated laboratory benchtop apparatus for capping and decapping laboratory sample storage tubes.

FIG. 1 illustrates a benchtop capper/decapper apparatus 10 for automated sample management. The capper/decapper apparatus 10 includes a deck 12 with a tube storage rack nest 14 and a second nest 16. A header 20 is located on a carriage 22 of the apparatus 10, and a row of 12 rotatable fittings 26 are located on the header 20. FIG. 1 shows adapter bits 28 mounted on the fittings 26. A touch screen 18 is used by the operator to program and control the operation of the apparatus 10. The apparatus 10 includes a drive mechanism to move the carriage 22 and the header 20 vertically along a Z-axis according to instructions programmed into the system. A drive mechanism in the apparatus 10 moves the deck 12 horizontally along a Y-axis.

In FIG. 1, an SBS-formatted, 96-tube storage rack 22 is set into the nest 14 on the deck 12. The tube storage rack 22 contains 96 sample tubes 56 in an 8×12 array, each with a screw cap 54. Nest 14 is on a turntable and is rotatable to change the orientation of the tube storage rack 22 in order to facilitate robotic handling of the rack in the laboratory. A screw cap cache rack 24 is located in the second nest 16 on the deck 12. The cache rack 24 includes 96 receptacles in an 8×12 array, and is designed to hold one or more rows of screw caps that have been removed from the respective sample storage tubes.

Individual screw motors in the carriage 22 rotate the fittings 26 and the adapter bits 28 in order to screw caps onto the sample storage tubes and screw caps off of sample storage tubes. When the carriage 22 and header 20 are lowered with a set of adapter bits 28 mounted on the fittings 26 against a row of caps 54, each individual screw motor rotates very slowly in the clockwise direction (i.e., tightening rotation) as the header 20 applies slight downward pressure until the adapter bit 28 finds the proper mating orientation for the head on the respective cap, at which point the bit 28 slides into the head of the cap 54. Each screw motor has torque sensing so that once it finds the proper orientation and drops in to mate with the head of the cap, it stops rotating until all bits 28 are aligned and ready to be fully inserted. Generally speaking, all adapter bits 28 do not drop in at once because it is unlikely that the entire row of caps will have the exact same rotational orientation in the rack. The slow rotation enables the adapter bits 28 to reliably mate with the heads on the caps 54. Once fully inserted, the apparatus controls the rotation of the screw motors in the counter clockwise direction (loosening direction) to screw the caps off the sample tubes. The apparatus then lifts the caps, moves the deck 12 so that an appropriate row in the cache rack 24 is located below the header 20 and lowers the caps into an empty row on the cache rack 24. The cache rack 24 may include specialized receptacles to hold the caps 54 when the adapter bits 28 are lifted. When the caps 54 are returned and screwed on to the row of tubes in the tube storage rack 54, the torque sensors ensure that the caps 58 are not overtightened.

A laser sensor 30 is used to sense whether adapter bits 28 are mounted on the fittings 26. The laser sensor 30 is also used to determine whether labware such as the racks or a row of sample tubes is in place prior to executing automation steps. The apparatus 10 also includes a 2-D bar code reader and a 1-D bar code reader (not shown). A window 32 on the base of the apparatus 10 enables a 2-D bar code reader to view the bottom of storage tubes held in the rack 22. An angled mirror (now shown) allows the 1-D bar code reader to read bar codes on the side walls of the racks 22, 24. The benchtop apparatus 10 shown in FIG. 1 is a stand alone unit; however, those skilled in the art will understand that it can be mechanically integrated for use with automated fluid handling equipment.

Referring still to the exemplary embodiment in FIG. 1, the bit adapters 28 can be attached or removed to the fittings 26 manually, or in accordance with the invention the entire row of adapter bits 28 can be changed automatically. Changing of the adapter bits 28 is necessary, for example, when screw caps must be removed from a different brand of sample storage tubes.

Figure 2:
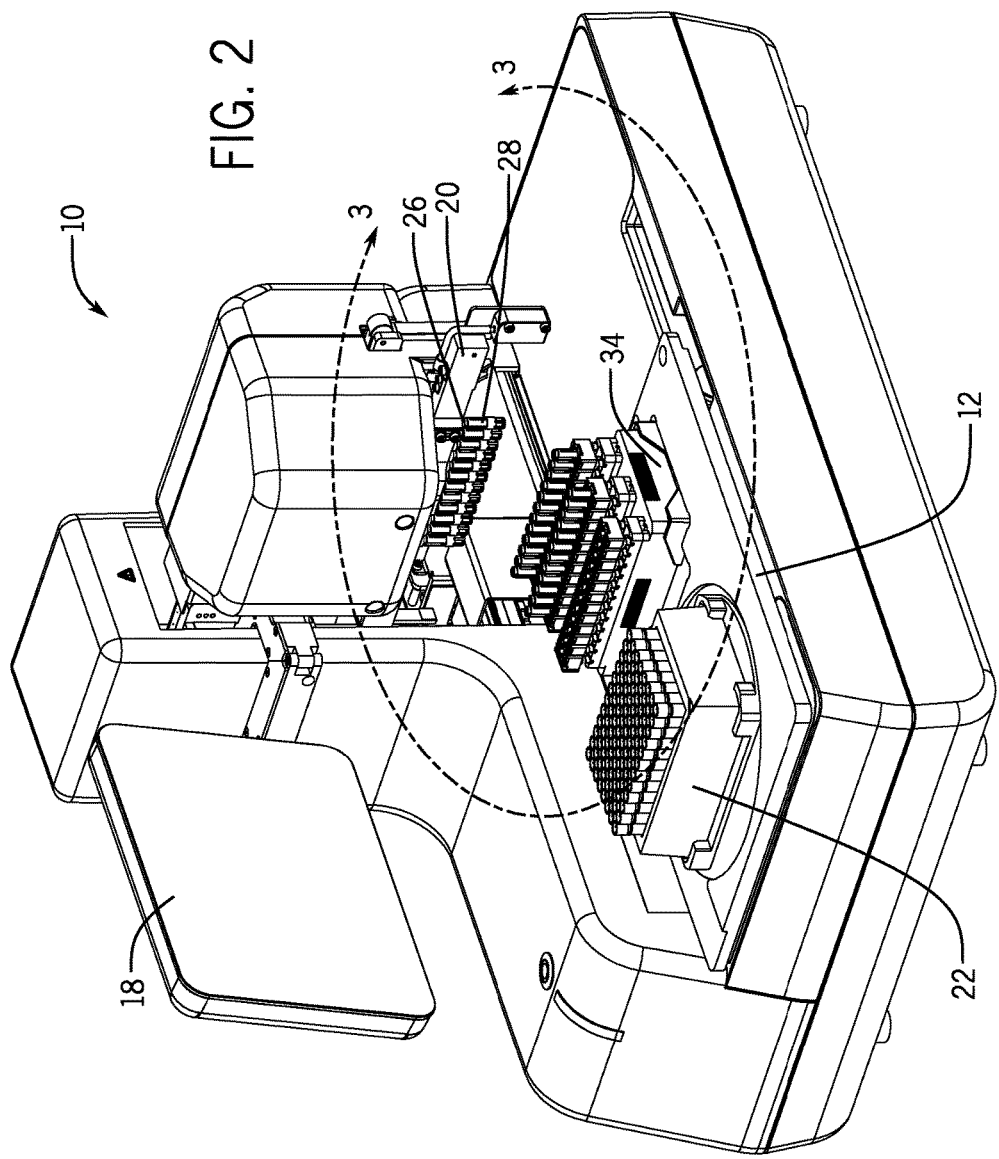
FIG. 2 is a view similar to FIG. 1 showing a bit exchange magazine assembly constructed in accordance with an exemplary embodiment of the invention located in a nest on a deck of the apparatus.
Figure 3:
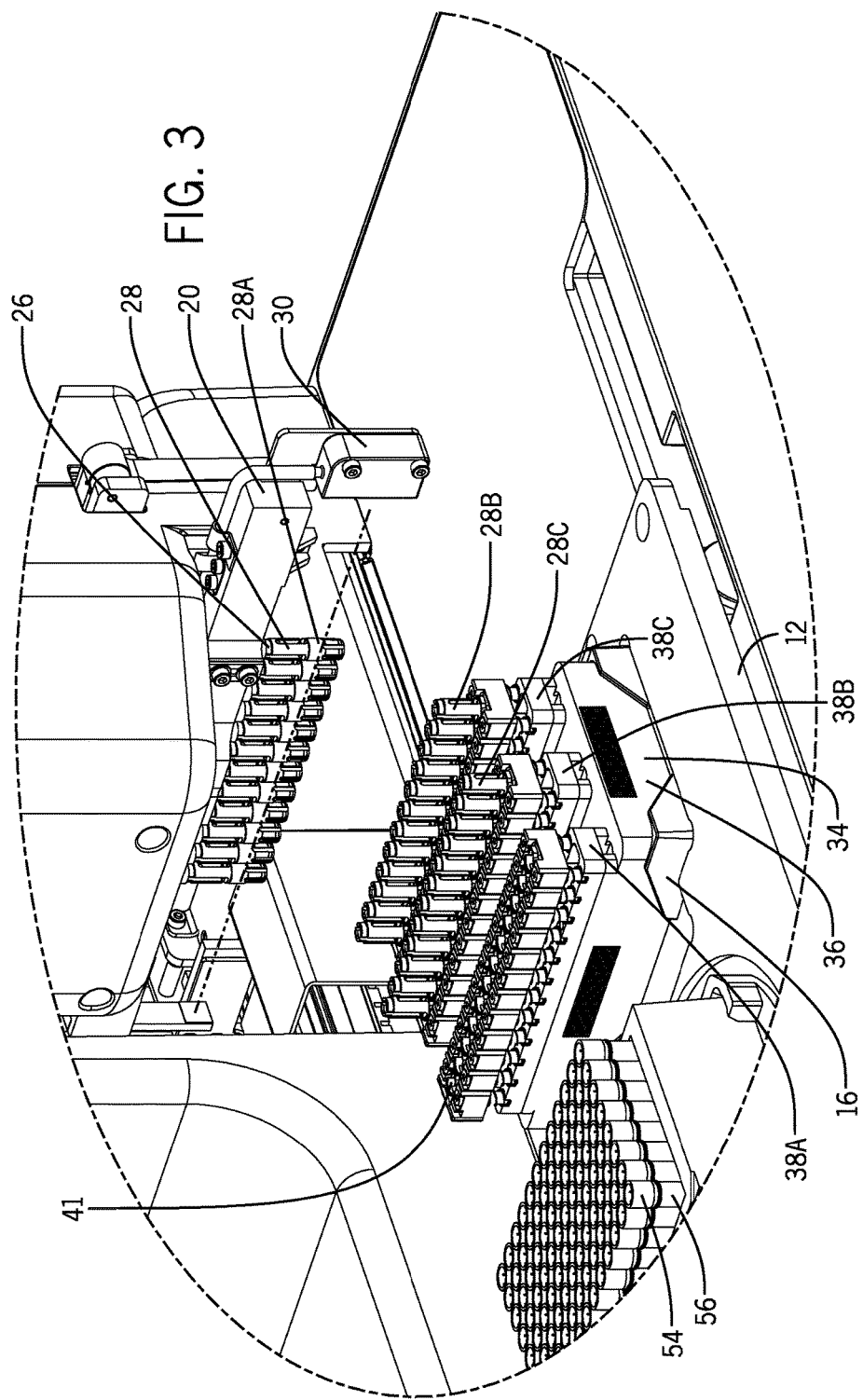
FIG. 3 is a detailed view of the area identified by line 3-3 in FIG. 2.

In FIG. 2, the screw cap cache rack 24 (FIG. 1) is replaced with a bit exchange magazine assembly 34 in order to start the bit exchange procedure. FIG. 3 shows the bit exchange magazine assembly 34 in more detail. It comprises an SBS-formatted magazine adapter block 36 that is set into the second nest 16 on the deck 12. Three bit magazines 38A, 38B and 38C are mounted to a top surface of the magazine adapter block 36. Each bit magazine 38 includes a row of receptacles 41 for holding a set of adapter bits 28A, 28B and 28C. In FIG. 3, the first bit magazine 38A is empty, and the bits 28A that are to be stored in the first magazine 38A are mounted on the fittings 26 on the header 20. Typically, the configuration of the heads of the bits for the first bit magazine 38A will be different from the configuration of the heads of the bits for the second magazine 38B and the third magazine 38C. Although FIGS. 2 and 3 show the bit exchange magazine assembly 34 having three bit magazines 38A, 38B and 38C mounted on the block 36, the invention can also be implemented with fewer than three bit magazines 38, or more, if the bit magazines can fit on the block 36. If only one bit magazine 38 is on the adapter block 36, then another assembly 34 must be placed in the nest 36 during the bit exchange process. In the configuration shown in FIG. 3, the adapter bits 28A are intended to be unloaded into the receptacles 40 in the first magazine 38A and then the adapter bits 28B or 28C from the magazines 38B or 38C or bit adapters on a different bit exchange magazine assembly 34 may be mounted onto the header 20.

FIGS. 4A through 4E show a variety of adapter bits 128A, 128B, 128C, 128D and 128E. Each bit 128A through 128E includes a collar 40, a torso 42A-42E and a bit head 44A-44E. The collars 40 on each of the bits 128A-128E have a common configuration in order to facilitate mounting to the fittings 26 on the header 20. The fittings 26 have a pin and spring mounting mechanism, see for example FIG. 11. The bit collar 40 includes a pin receiving channel 46 on each side of the bit 128A-E. The pin receiving channel 46 includes an access portion 48 that extends from the top of the collar 40 vertically downward. The pin receiving channel 46 also includes a locking portion 50 that is rotationally offset from the access portion 48. The locking portion 50 extends vertically but stops before reaching the top of the collar 40 in order to secure the respective pin on the fitting 26 in the locking portion 50 when the bit 128A-E is mounted on the fitting. A turning portion 52 connects the bottom of the access portion 48 to the bottom of the locking portion 50.

Figure 4A:
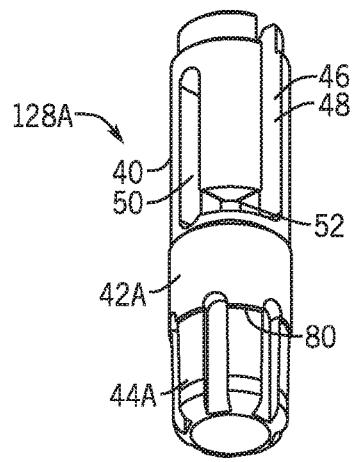
FIGS. 4A through 4E are detailed views of various adapter bits used in connection with the invention.
Figure 4B:
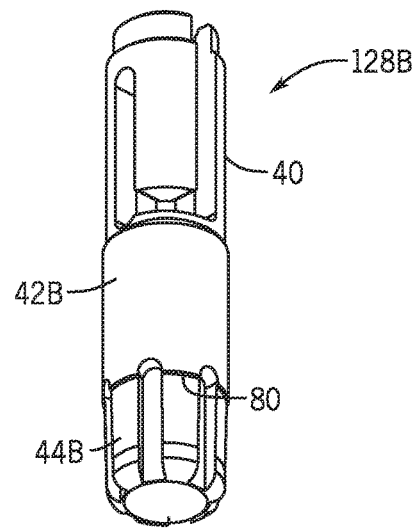
Figure 4C:
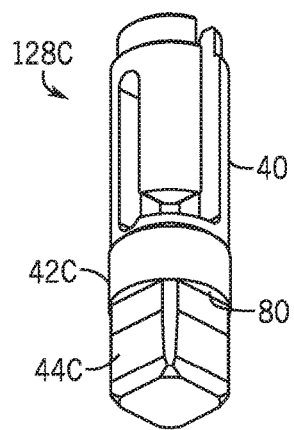
Figure 4D:
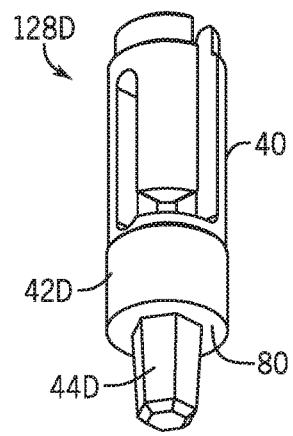
Figure 4E:
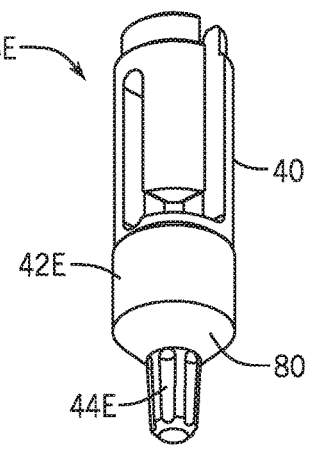

The configuration of the head 44A of bit 128A in FIG. 4A is the same as the configuration on the head 44B of the bit 128B in FIG. 4B; however, the central torso 42B of bit 128B is longer than the central torso 42A of bit 128A. The longer torso 42B on bit 128B is useful for capping or decapping large format sample tubes or vials such as those stored in a 48-channel format or a 24-channel format. The head configurations in FIGS. 4A and 4B are different from the head configurations shown in FIGS. 4C, 4D and 4E. Each head 44A and 44B, 44C, 44D and 44E is designed, as mentioned, to fit into a mating configuration for the screw caps 54 on the sample tubes 56, see for example FIG. 3. The adapter bits 128A-128E may be constructed out of any suitable material such as milled aluminum with a powder coating.

Figure 8:
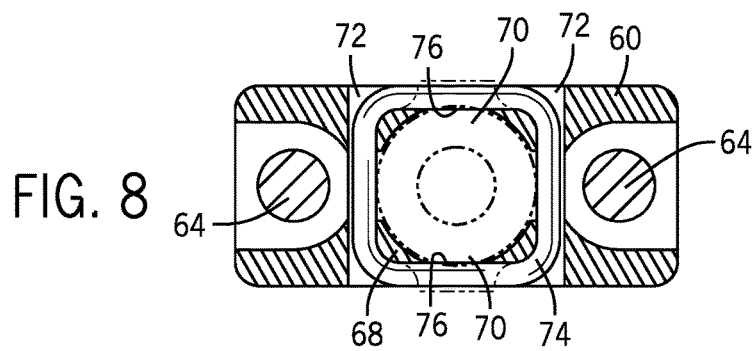
FIG. 8 is a cross sectional view taken along line 8-8 in FIG. 7.

Referring to FIGS. 5 and 6, the magazine adapter block 36 can be made of aluminum and is sized to fit an SBS-formatted nest. A longitudinal base member 58 is mounted on the block 36 to form the base for the respective bit magazine 38. The bit receptacle 41 is contained in a floating receptacle member 60 that is mounted with stop screws 62 on steel stanchions 64. The steel stanchions 64 are mounted through openings in the longitudinal base member 58 to the block 36. Compression springs 66 are placed over the stanchions 64 in order to support the floating receptacle member 60. An upstanding wall 68 on the top of the member 60 forms the bit receptacle 41 with a general cylindrical shape. The upstanding sidewall 68 includes openings 70. A retaining notch 72 on a top surface of the floating receptacle member 60 surrounds the upstanding receptacle wall 68, and retention clasp 74 is secured in the notch 72 around the upstanding receptacle wall 68. The retention clasp 74, as shown best in FIGS. 6 and 8, has a generally square shape. Referring in particular to FIG. 8, the lengths of the clasp 74 between its corners extend across the openings 70 in the receptacle wall 68 to provide friction retention surfaces 76. The perpendicular distance between opposing retention surfaces 76 is slightly less than the diameter across the otherwise cylindrical inner surface of the receptacle wall 68. The torso 42 of the adapter bit 28 is secured by friction by the retention surfaces 76 on the retention clasp 74 when the bit 28 is placed in the receptacle 40.

FIG. 5 shows the floating receptacle member 60 and retention clasp 74 attached to the base 58 over stanchion 64 and supported by spring 66. In FIG. 5, the adapter bit 28A is shown above the receptacle 41 for purposes of illustration, whereas adapter bits 28B, C, etc. are shown loaded in the magazine 38. It should be understood that in practice, all of the bits 28A, 28B, 28C for respective magazine 38A, 38B or 38C are loaded into the row of receptacles or removed from the row of receptacles together and not individually.

Figure 7:
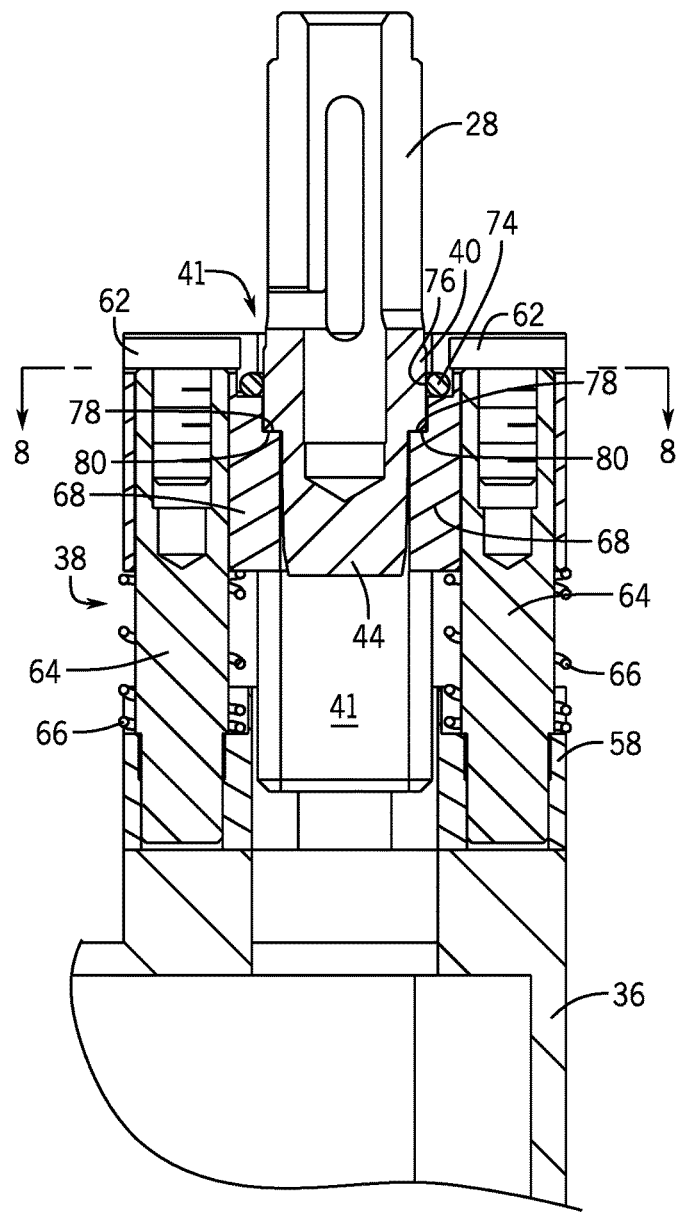
FIG. 7 is a sectional view taken through one of the receptacles in the bit exchange magazine assembly.

Referring to FIG. 7, the sectional view shows an adapter bit 28 loaded into a receptacle 41 on the magazine 38. As noted before, the friction retention surfaces 76 on the retention clasp 74 engage the torso 42 of the adapter bit 28. The head 44 of the adapter bit 28 is located within the receptacle 41 and there is space below the head 44 in the receptacle 41. The receptacle 41 is designed to fit a wide variety of adapter bits 28, including adapter bits in which the torso 42 is short, e.g. 42A in FIG. 4A, or longer, e.g. torso 42B in FIG. 4B; or adapter bits 28 in which the head 44 is longer or shorter as well. The collar 40 on the adapter bit 28 and the diameter of the torso 42 on the adapter bit 28, however, are consistent in configuration and dimension in order to facilitate engagement and disengagement from the fittings 26 on the header 20.

Figure 9:
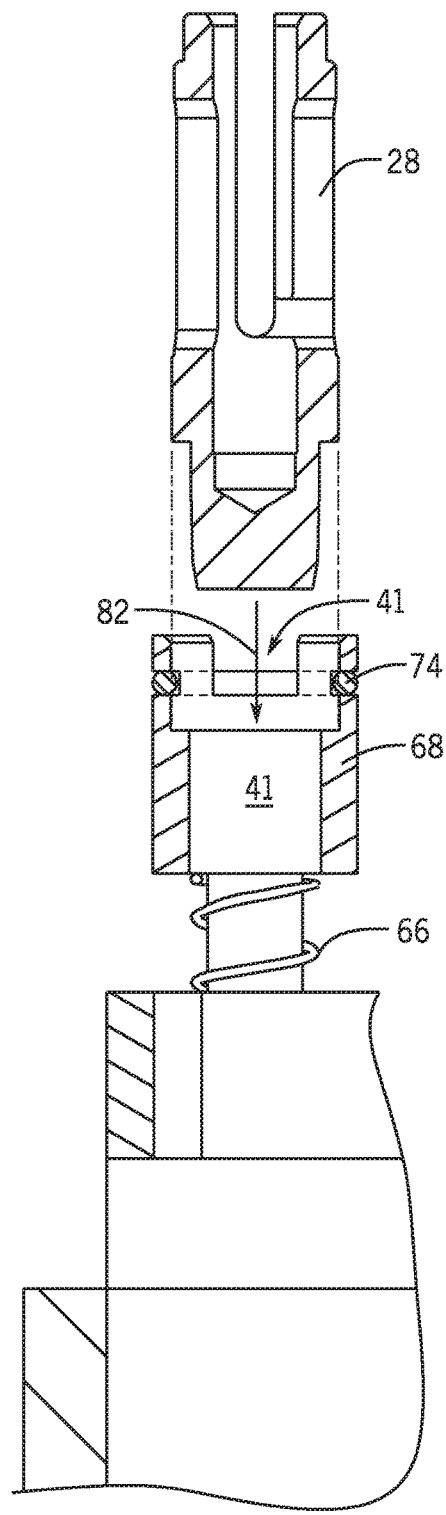
FIG. 9 is a schematic view showing an adapter bit before it is inserted into a bit receptacle on the bit exchange magazine assembly.
Figure 10:
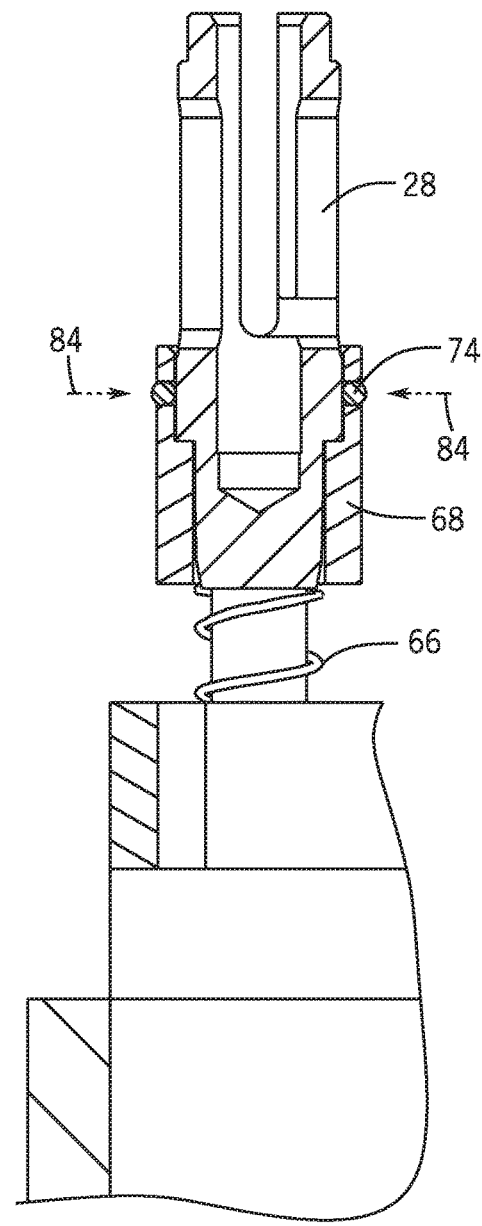
FIG. 10 is a schematic view similar to FIG. 9 showing the adapter bit fully inserted into the bit receptacle.

The receptacle wall 68 includes a stepped shoulder 78, and the adapter bit 28 has a narrowing shoulder 80 in the transition between the torso 42 and the head 44. The narrowing shoulder 80 on the adapter bit 28 engages the stepped shoulder 78 on the floating receptacle member 60 when the bit 28 is inserted into the receptacle 41. The retention clasp 74 is located slightly above the stepped shoulder 80 on the floating receptacle member 60, and it is at this location as mentioned previously that the friction surfaces 76 on the retention clasp 74 hold the bit 28 in place in the magazine 38. Desirably, the adapter bits 28 should stay in place even when the assembly 34 is tilted 180°. The friction should prevent the adapter bits 28 from falling out of the magazine 38 when the fittings 26 are pulled upward after offloading a set of bits 28 into the magazine 38. The system desirably includes a stripper bar (not shown) which presses down on top of the bits 28 in an offloaded row to ensure all the bits 28 are fully inserted into the receptacles 41 in the magazine 38. The spring 66 mechanism absorbs height tolerances between the fittings 26 and the adapter bits 28 and the magazine 38. Referring to FIGS. 9 and 10, the bit 28 on a fitting 26 (FIG. 11) is moved downward as depicted by arrow 82 into receptacle 41 to unload the bit 28. Once the bit 28 is fully inserted into the receptacle 41 normal forces and friction forces from the retention clasp 74 as shown by arrows 84 (FIG. 10) hold the bit 28 in place in the receptacle 41. The forces depicted by arrows 84 should have sufficient magnitude to prevent rotation of the bit 28 when it is mounted in the receptacle 41.

FIG. 11 illustrates a fitting 26 on the header 20 onto which the collar 40 of the adapter bit 28 is mounted. The fitting 26 includes a mounting shaft 86 that is generally cylindrical and extends vertically. A horizontal cylindrical pin 88 extends through the mounting shaft 86 and extends outward from the shaft 86 on opposing sides of the shaft. A spring biased mounting sleeve 90 is provided on the header at the base of the mounting shaft 86. In order to mount the adapter bit 28 on the mounting shaft 86, the pins 88 on the mounting shaft 86 are aligned with the pin receiving channels 46 on the collar 40 of the bit 28. The mounting shaft 86 is inserted into the collar 40 such that the rim 92 of the collar 40 presses against a bottom edge 94 of the spring bias mounting sleeve 90. The mounting shaft 86 is further inserted against the spring bias of the mounting sleeve 90 until the pins 88 reach the bottom of the access portion 48 of the pin receiving channels 46. At that point, either the mounting shaft 86 is rotated (for automatic attachment) or the bit 28 is rotated (for manual attachment) to move the pin through turning portion 52 of the pin receiving channel 46 so that the pins 88 reside at the bottom of the locking portion 50 of the pin receiving channel 46. The spring bias of the mounting sleeve 90 then pushes the bit collar 40 downward to move the pins 88 to the top of the locking portion 50 of the pin receiving channels 46. When a bit is mounted manually, the user releases the bit after it has been turned so that the spring bias of the mounting sleeve 90 immediately pushes the bit 28 downward to lock the bit on the mounting shaft 86. The automated procedure for offloading and mounting bits 28 is described in connection with FIGS. 12A through 12G.

Figure 12B:
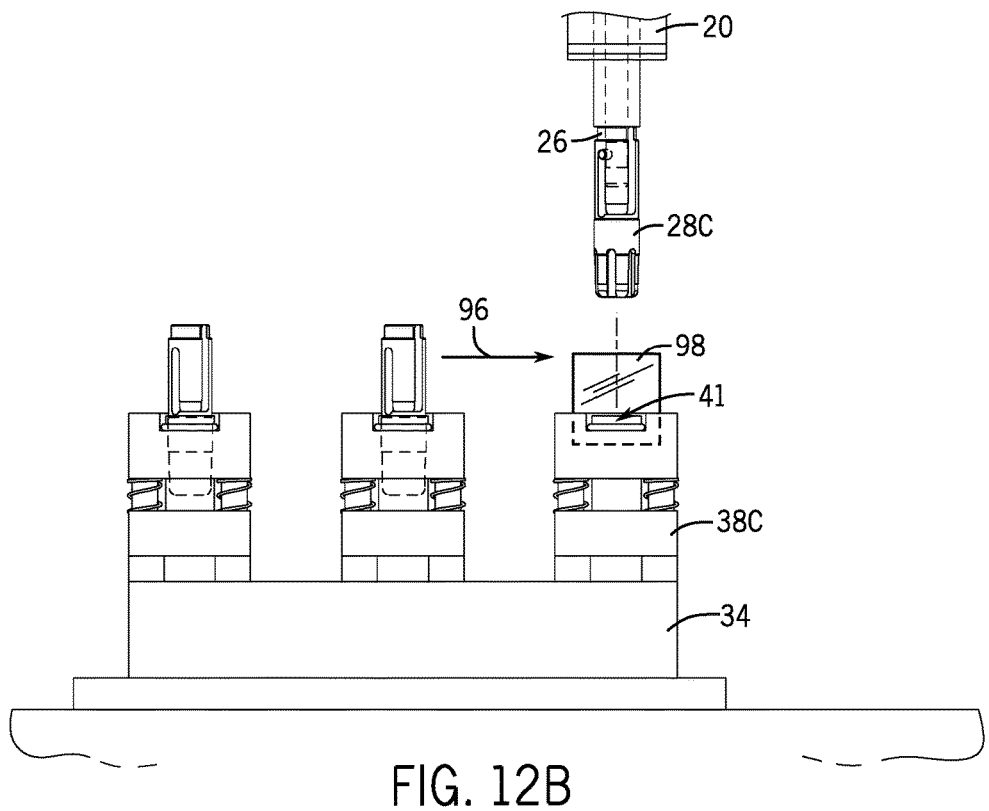

FIGS. 12A to 12F illustrate steps involved to automatically unload the bits. In FIG. 12A, one adapter bit 28A, 28B, 28C is shown to represent each set of adapter bits. It should be understood that the operation of the header 20 simultaneously loads and unloads each bit 28 of the set simultaneously. FIG. 12A shows the bit 28C on the fitting 26 extending downward from the header 20. The spring biased collar 90 presses the bit 28C downward so that the pin 88 on the fitting is securely locked in the locking portion 50 of the pin receiving channel 46. Arrow 96 indicates that the deck 12 and the magazine assembly 34 need to be moved to locate magazine 38C under the fittings 26 on the header 20 and the attached bits 28C in order to remove the bits 28C. FIG. 12B shows the assembly 34 after the deck 12 and assembly 34 have been moved in accordance with arrow 96 so that the magazine 38 resides below the header 20, the fittings 26 and the attached adapter bits 28C. FIG. 12B also identifies reflector strip 98 which is used for a laser sensor 30 (see FIG. 3). The laser sensor 30 can be used to detect whether the receptacles 41 in the magazine 38 are empty and ready to receive adapter bits 28C. The laser sensor 30 can also be used for example in FIG. 12A to detect the presence of adapter bits 28C on the fittings 26, or even to determine whether an assembly 34 is located in the appropriate location prior to a loading or unloading sequence. The laser sensor is additionally used to scan reflector codes that are used to label each of the different rows of adapter receptacles to identify which adapter type is associated with that particular row.

Figure 12C:
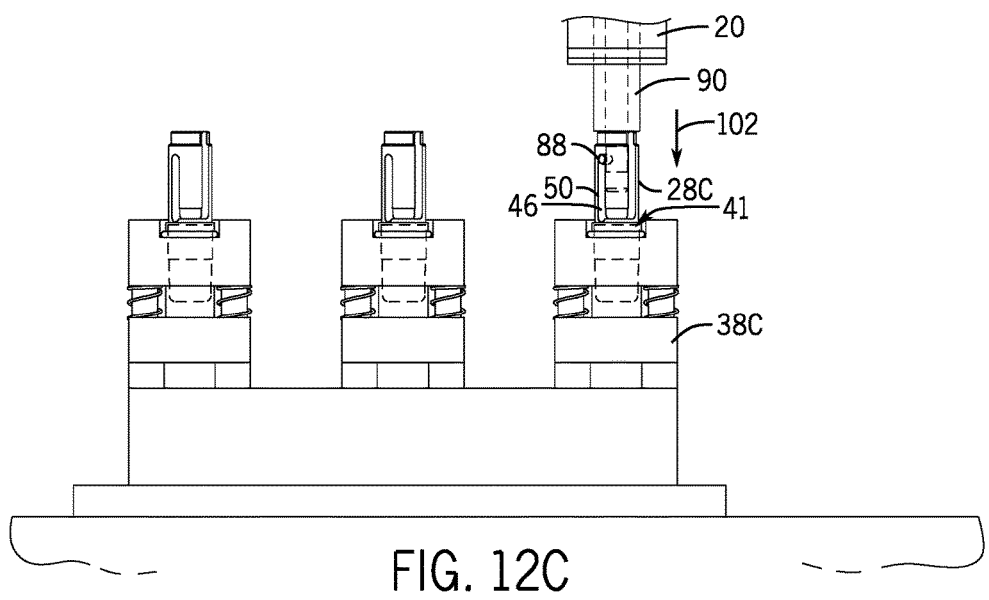
Figure 12D:
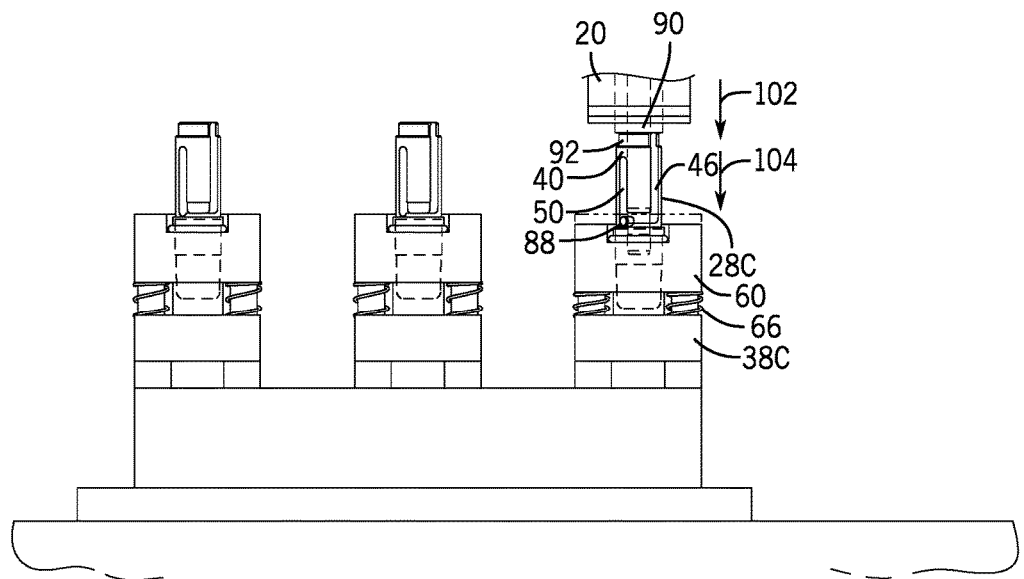
Figure 12E:
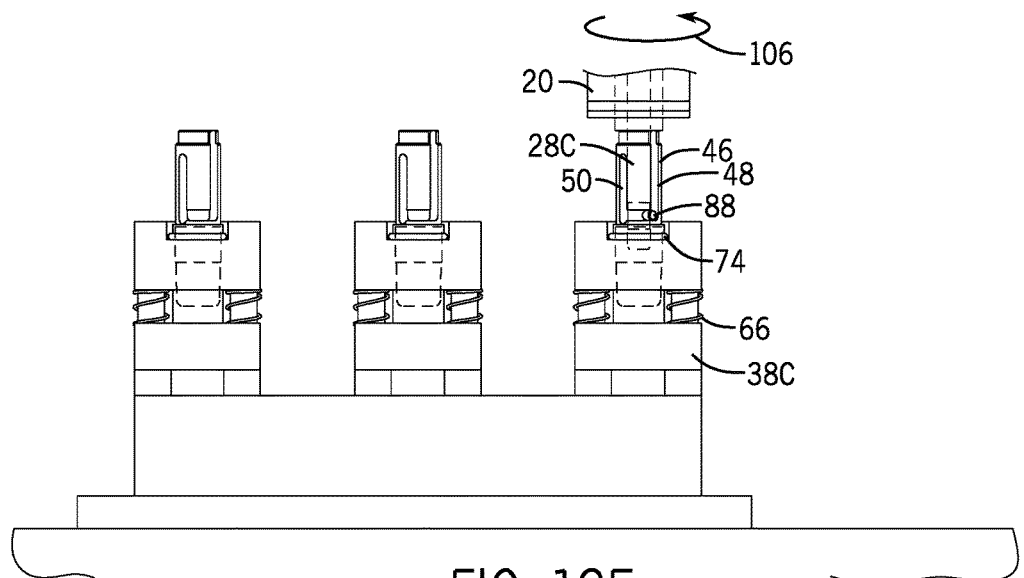
Figure 12F:
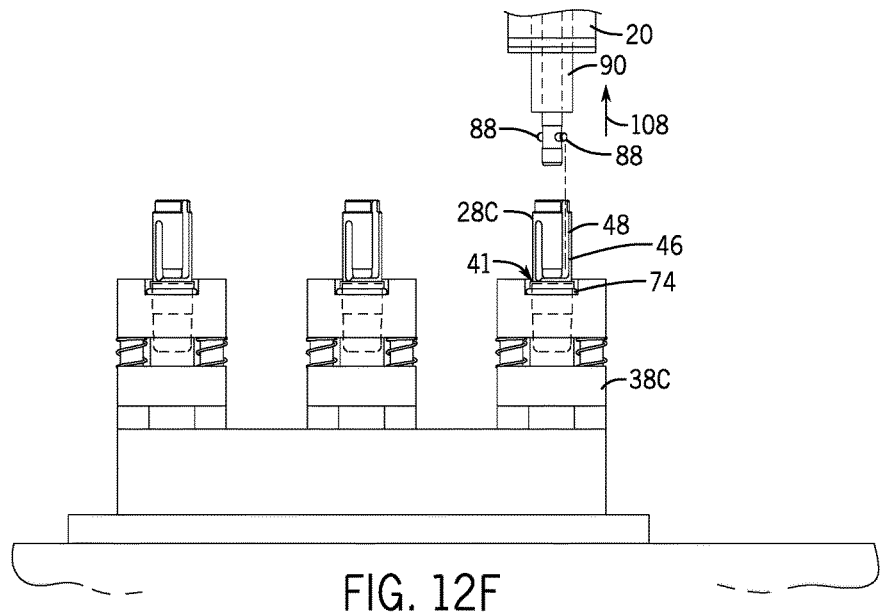

FIG. 12C illustrates the header 20 moving downward in the direction shown by arrow 102 to insert the adapter bit 28C into the receptacle 41 on the magazine 38C. FIG. 12D shows the next step in the process in which the header 20 has moved down further as indicated by both arrows 102 and 104. The additional downward motion between FIGS. 12C and 12D corresponds to downward motion of the header 20 after the bit 28C has been fully inserted into the receptacle 41 on the magazine 38C. FIG. 12C shows the bit 28C inserted into the receptacle 41 at the same position as it is shown in FIG. 7 with the narrowing shoulder 80 on the bit 28C engaging the stepped shoulder 78 on the receptacle wall 68. In FIG. 12D, the nose 92 of the collar 40 pushes against the spring mounted sleeve 90 to compress the springs while the fitting 26 and pin 88 on the fitting move downward through the locking portion 50 of the pin receiving channel 46. FIG. 12D also shows springs 66 supporting the floating receptacle member 60 as slightly compressed. Referring now to FIG. 12E, the retention clasp 74 holds the bit 28C from rotating. With the pin 88 at the bottom of the locking portion 50 of the pin receiving channel 46, the header 20 is rotated as shown by arrow 106. This rotation moves the pin 88 from the bottom of the locking portion of the pin receiving channel 46 to the bottom of the access portion 48 of the pin receiving channel 46. FIG. 12F shows the header 20 and fitting 26 moved upward as shown by arrow 108 so that the pin 88 exits from the access portion 48 of the pin receiving channel 46 and the fitting 26 clears the bit 28C leaving the bit 28C in the respective receptacles in the magazine 38C.

Figure 12G:
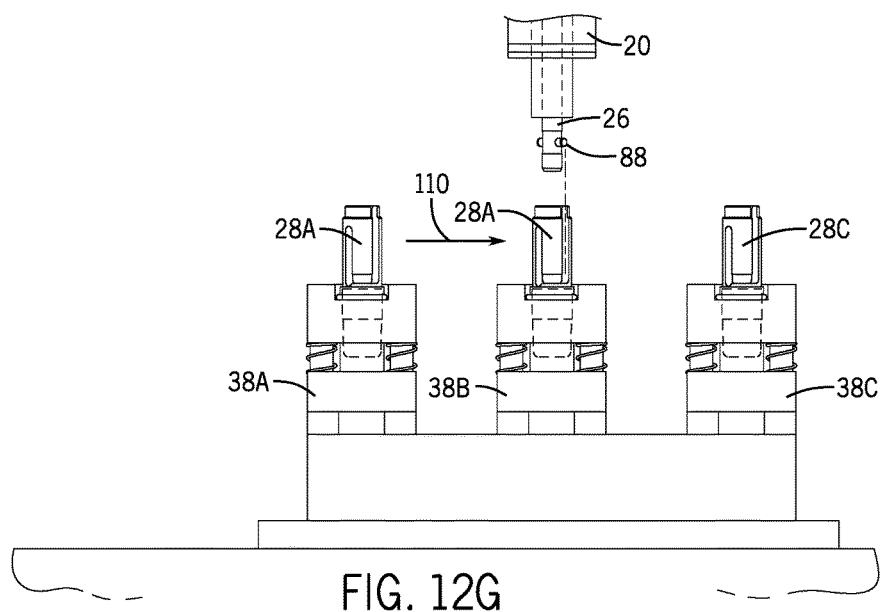

FIG. 12G shows the deck 12 and the magazine assembly 34 moved in accordance with arrow 110 so that the header 20 and the fittings 26 are generally aligned over the adapter bits 28B in magazine 38B. For automatic attachment, the header 290 moves downward so that the pin 88 applies slight pressure against the top of the bit collar 40. The individual screw motors in the carriage 22 rotate the fittings 26 slowly as the header 20 applies slight downward pressure until the pins 88 on the fitting shafts 86 find the access portion 48 of the respective pin receiving channel 46, at which point the shaft 86 and pin 88 slide into the access portion 48 of the pin receiving channel 46 on the bit 28. Once each screw motor has torque sensing, pin 88 drops in to collar 40 once it finds the proper orientation and stops rotating until all bits 28 are aligned and ready to be fully inserted. All shafts 86 and pins 88 do not drop in at once because it is unlikely that the entire row bits 28 will have the exact same rotational orientation in the rack. Once all the pins 88 are located in the respective pin receiving channels 46, the procedure for mounting the adapter bits 28B on the fittings 26 is similar but in reverse to the steps described in FIGS. 12A-12F for unloading a set of bits into the respective magazine. With the new set of adapter bits 28A, 28B or 28C mounted on the fittings 26 the system is ready for use to cap or decap sample tubes having heads with the new configuration.

The user interface accessed through the touch screen 18 desirably enables the user to choose whether to replace the adapter bits 28 manually or automatically. If automatic, the laser sensor is used to verify the identity of the adapter bits on the magazine adapter block assembly 34 and display the identification of the bits on the touch screen 18.

In the foregoing description, certain terms have been used for brevity, clarity, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. For example, the exemplary benchtop apparatus 10 shown in the figures screws off or screws on caps one row of sample tubes at a time; however, it is also contemplated that the invention may be used in connection with systems configured to screw on or screw off an array of caps (e.g., 96 caps in an 8×12 array) contemporaneously, or even a single cap at a time.

It is to be expected that various equivalents, alternatives and modifications are possible within the scope of the appended claims. Each limitation in the appended claims is intended to invoke interpretation under 35 U.S.C. §112, sixth paragraph, only if the terms "means for" or "step for" are explicitly recited in the respective limitation.

What is claimed is:

1. An automated apparatus for screwing caps on laboratory sample tubes or screwing caps off of laboratory sample tubes or both, said apparatus comprising:
a deck containing at least one nest for holding a tube storage rack in a set position so that rows of tube receptacles in the tube storage rack set in the nest are parallel to each other and extend in a first direction;
a header located above the deck and oriented parallel to the first direction, the header being capable of moving at least vertically up and down with respect to the deck;
at least one set of adapter bits;
multiple fittings on the header for receiving the set of adapter bits with each bit being mounted to a respective fitting, said bits being configured to engage a head of a cap for a respective laboratory sample tube and turn the cap with respect to the sample tube when the sample tube is set within the tube receptacle in a tube storage rack positioned in the nest;
at least one motor for turning the multiple fittings and adapter bits mounted on the fittings and any cap engaged by the respective bit;
a bit exchange magazine assembly; and
at least one row of bit receptacles on the magazine assembly that are arranged to be parallel with the first direction when the bit exchange magazine assembly is set in the nest.

2. The apparatus as recited in claim 1 wherein the bit exchange magazine assembly has at least two rows of bit receptacles that are arranged to be parallel with the first direction when the bit exchange magazine assembly is set in the nest.

3. The apparatus as recited in claim 2 wherein the set of adapter bits are a first set of adapter bits each having a head with a first combination of head configuration, head size and torso length and the apparatus further comprises a second set of bits each having a second combination of head configuration, head size and torso length.

4. The apparatus as recited in claim 1 wherein the bit exchange magazine assembly has at least three rows of bit receptacles that are arranged to be parallel with the first direction when the bit exchange magazine assembly is set in the nest.

5. The apparatus as recited in claim 1 wherein each of the fittings on the header has a spring and pin mechanism and the adapter bits include a collar into which the respective fitting is pushed in order to mount the adapter bit, said collar having a pin receiving channel that receives the pin and is configured to include a first rotational pin position in which the pin locks the bit on the fitting against spring bias and a second rotational pin position in which the bit is released from the fitting by the spring bias.

6. The apparatus as recited in claim 1 wherein the bit receptacles on the bit exchange magazine assembly each include a retention clasp to releasably hold the respective adapter bit and prevent the bit from rotating within the receptacle.

7. The apparatus as recited in claim 1 further comprising a light sensor to detect whether the adapter bits are located on the header.

8. The apparatus as recited in claim 1 further comprising a light sensor to detect whether adapter bits are located in the bit exchange magazine assembly.

9. The apparatus as recited in claim 1 further comprising:
reflector strips defining a binary code associated with each row of bit receptacles on the bit exchange magazine assembly; and
a laser sensor used to read the binary code contained in the strip.

10. The apparatus as recited in claim 1 wherein the nest is dimensioned to hold a tube storage rack having an 85.44 mm by 127.76 mm footprint, and the bit exchange magazine assembly has an adapter block that is sized to fit in the nest.

11. The apparatus as recited in claim 10 wherein the fittings on the header are centerline spaced at 9 mm.

12. A method of automatically changing a set of adapter bits on a machine that screws caps on laboratory sample tubes or screws caps off of laboratory sample tubes or both, said method comprising the steps of:
providing a bit exchange magazine assembly, said bit exchange magazine assembly including at least two rows of bit receptacles that are arranged to be parallel with a first direction when the magazine assembly is set in a nest located on a deck of the machine that screws caps on laboratory sample tubes or screws caps off of laboratory sample tubes or both;
providing a header on the machine above the deck and orientated parallel to the first direction, the header including multiple fittings for receiving a set of adapter bits wherein each bit has a collar for positioning the bit to a respective fitting, and is further configured to engage a cap for a laboratory sample tube and turn the cap with respect to the sample tube when the sample tube is held in a tube storage rack positioned in the nest;
aligning the header with an empty first row of receptacles in the bit exchange magazine assembly located in the nest on the deck;
moving the header downwards so that the bits on the fittings push down into the empty first row of receptacles and move a pin on the respective fitting through a locking channel relative to the collar of the respective bit;
holding the adapter bits from turning within the receptacles;
turning the fittings to move the pin from a locked rotational position to an unlocked rotational position;
raising the header to move the pin on the respective fitting through an access channel relative to the collar of the respective bit leaving the set of adapter bits in the first row of receptacles in the magazine assembly;
aligning the header over a second row of receptacles in the bit exchange magazine assembly located in the nest, said second set of receptacles including another set of adapter bits;
moving the header vertically downward to push the fittings into the respective collars of the adapter bits in the second row of receptacles such that a pin on the respective fitting moves downward through an access channel relative to the collar of the respective bit;
continuing to hold the adapter bits in the second row of receptacles from turning;
turning the fittings to move the respective pins to a locked rotational position aligned with a locking channel in the respective adapter bit; and
raising the header to move the fittings and the respective adapter bits upward, leaving the second row of receptacles in the magazine assembly empty.

13. The method as recited in claim 12 further comprising the step of sensing whether a set of bits is located in the second row of receptacles on the bit exchange magazine assembly and whether the first row of receptacles on the bit exchange magazine assembly is empty.

14. The method as recited in claim 12 further comprising the step of reading binary codes associated with each respective row of receptacles on the bit exchange magazine assembly prior to exchanging bits.

15. The method as recited in claim 12 wherein the nest is dimensioned to hold a tube storage rack having an 85.44 mm by 127.76 mm footprint, and the bit exchange magazine assembly has an adapter block that is sized to fit in the nest.

16. The method as recited in claim 15 wherein the fittings on the header are centerline spaced at 9 mm.

* * * * *